United States Patent [19]

Volodchenko et al.

[11] Patent Number: 4,916,535
[45] Date of Patent: Apr. 10, 1990

[54] METHOD OF NON-DESTRUCTIVE QUALITY INSPECTION OF MATERIALS AND VIDEOMONITOR REALIZING THIS METHOD

[76] Inventors: Dmitry B. Volodchenko, ulitsa Novovilenskaya, 3, kv. 32; Valery S. Kozlov, Leninsky prospekt, 16, kv. 76., both of Minsk; Vladimir A. Troitsky, ulitsa Sapernoe pole, 26a, kv. 60, Kiev; Vladimir V. Kljuev, ulitsa 3 Frunzenskaya, 14, kv. 5, Moscow; Alexandr V. Stepanenko, ulitsa Surganova, 40, kv. 25, Minsk; Orest S. Semenov, ulitsa Verkhnava Pervomaiskaya, 53/35, korpus 3, kv. 27, Moscow; Jury K. Bondarenko, ulitsa Uritskogo, 31, kv. 37; Jury B. Eskov, ulitsa Surikova, 4, kv. 58, both of Kiev; Semen S. Kulev, Leninsky prospekt, 76a, kv. 39; Nikolai V. Kotov, ulitsa Kalinovskogo, 83, kv. 37, both of Minsk, all of U.S.S.R.

[21] Appl. No.: 82,386
[22] Filed: Aug. 6, 1987
[51] Int. Cl.4 .............................................. H04N 7/18
[52] U.S. Cl. ..................... 358/101; 358/106
[58] Field of Search .............. 358/101, 106, 107, 112; 382/8; 324/213; 356/237

[56] References Cited

U.S. PATENT DOCUMENTS 4,541,011 9/1985 Mayer et al. .......................... 358/106
4,568,971 2/1986 Alzmann et al. ..................... 358/101
4,583,181 4/1986 Gerber et al. ................... 358/106 X
4,596,037 6/1986 Bouchard et al. ............... 358/107 X
4,668,982 5/1987 Tinnerino ....................... 358/106 X

OTHER PUBLICATIONS

USSR Inventor's Certificate #456572, 1974.
"Forming Television Signals in Flaw Detectors Using Automatic Mechanical Scanning"; Defektoskopia; 1979; #5, pp. 106-109.
Booklet of Krautkramer, Production Program for 1984-1985, p. 7-No translation, Nov. '84.

Primary Examiner—James J. Groody
Assistant Examiner—Victor R. Kostak
Attorney, Agent, or Firm—Lilling & Greenspan

[57] ABSTRACT

A method of non-destructive quality inspection of materials wherein a data transmitter and a material to be inspected are positioned very near to each other and set in motion in relation to each other. Information fed by the data transmitter is converted into a black-white or color image indicative of the quality of the material being inspected. Information fed by the data transmitter is kept in a memory and, as it is converted into a black-and-white or color image, it is periodically read out. The address of a memory location in the memory from which the readout cycle is to begin is assigned prior to the start of each readout cycle. A videomonitor realizing this method including a data transmitter mounted on a scanning device, a display unit connected to a control unit and an address unit including a recording counter series connected to a switch, as well as a readout counter connected to another input of the switch. An address code rewrite unit is inserted between the output of the recording counter and the input of the readout counter.

10 Claims, 5 Drawing Sheets

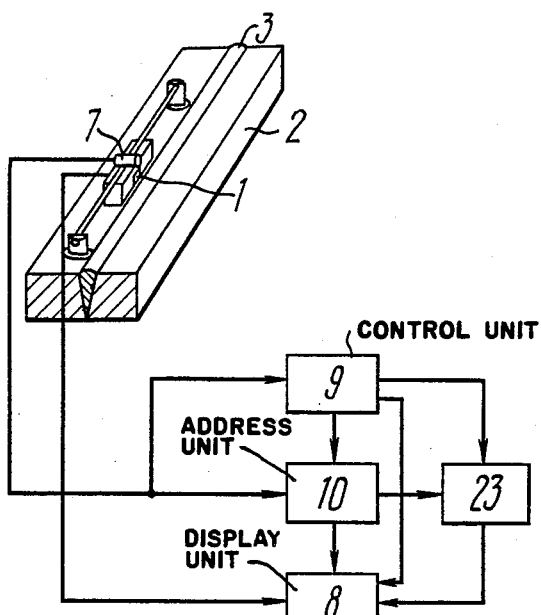
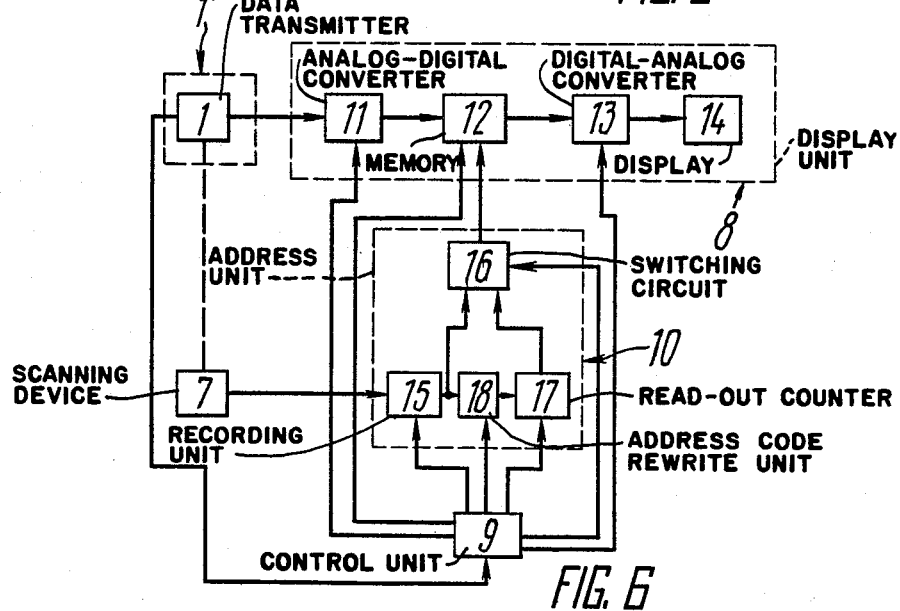

METHOD OF NON-DESTRUCTIVE QUALITY INSPECTION OF MATERIALS AND VIDEOMONITOR REALIZING THIS METHOD

BACKGROUND OF THE INVENTION

1. Field of the Invention

This invention relates to control and measuring instruments and, in particular, to methods and videomonitors for non-destructive quality inspection of materials.

The invention can be used in the oil and gas industry for pipe weld quality testing, in machine building for detecting flaws in rolled products, in ship building for quality testing of welded ship hulls and tanks, and in other fields where products have to be tested for continuity defects. It can also be employed in medicine and biology for storage, processing, and visualization of information on biological objects.

2. Description of the Prior Art

Known in the art is a method for non-destructive quality inspection of materials (U.S. Pat. No. 3,341,771; Cl. 324–213), comprising the steps of magnetizing the material to be inspected, a magnetic recording medium being placed on the surface on this material, then removing said magnetic medium which through the action of the magnetizing field had recorded a magnetogram which contains information on the quality of the material being tested, and placing the magnetic medium into a device for recording said magnetogram, in which the pick-up is positioned near the surface of the magnetic medium and their relative motion is ensured. Information sensed by the pick-up is converted into electrical signals which are used to assess the quality of the material.

The apparatus realizing this method comprises a magnetic pick-up capable of reciprocating motion above the surface of the magnetic medium, an amplifier, and an indicator. The indicator is a cathode-ray tube displaying a pulse signal whose shape is used to assess the quality of the material being inspected.

However, this method and apparatus realizing the method are deficient in that they can only be used to detect a flaw in the material being inspected. They cannot furnish any 3-D characteristics of this flaw, such as the depth, shape, length, relative position.

Also known in the art is an ultrasonic flaw detector USD1 manufactured by KRAUTKRÄMER in the Federal Republic of Germany "(Booklet of Krautkrämer, Production Program for 1984–1985, p.7)". In this device a data transmitter is an ultrasonic transducer placed on the surface of the material to be tested and their relative motion is ensured. Information fed by the transmitter is processed in the built-in microcomputer and displayed on the screen of the cathode-ray tube as an image of echo signals and as digital data on the depth of the flaw and the distance from the transducer to the projection of the flaw on the surface of the tested product.

But the aforementioned device is deficient in that it cannot provide a shadow-color image indicative of the quality of the material being tested. It also cannot provide prompt information on the amount and relative position of flaws in the material, their length and configuration.

The closest prior art is a method for non-destructive testing (cf., for example, U.S.S.R. Inventor's Certificate No. 456,572; 1974) whereby information fed by a pick-up, which is indicative of the quality of the material being tested, is subjected to scale and time conversion by entering this information to a storage unit in synchronism with the motion of the pick-up relative to the tested material, and then displayed on the screen of a cathode-ray tube, while the recording is simultaneously read from the memory.

There is known a videomonitor realizing this method (cf., for example, G. R. Kreps, Forming Television Signals in Flaw Detectors Using Automatic Mechanical Scanning, Defektoskopiya, 1979, No. 6, pp. 106–109) which comprises several series-connected components: a data transmitter mounted on a device which scans this transmitter in relation to the tested material, an analog-digital converter, a memory, a digital-analog converter, and a display which is a color electron beam tube; a recording counter connected in series to a switch whose output is connected to the memory, a readout counter whose output is connected to a second input of the switch, a control unit connected to the synchronization input of the data transmitter and to inputs of the recording counter, the readout counter, the analog-digital converter, the memory, the switch, and the digital-analog converter, a synchronization output of the scanning device being connected to the other input of the recording counter.

However, the aforementioned device is deficient in that it cannot provide continuous display of information on the quality of the tested material when the pick-up is transported in relation to this tested material for a long distance. This device also cannot provide a prompt increase in the resolution of the color picture for the detailed analysis of the material quality. It also cannot help determine precisely the coordinates and length of a defect.

The term "data transmitter" used here and henceforth in this description means a flaw detector equipped with a pickup. It is evident that the pickup is placed near the surface of the tested material on a scanning device, while information and timing signals are fed from the outputs of the flaw detector.

SUMMARY OF THE INVENTION

The primary object of this invention is to provide a method of non-destructive quality inspection of materials, which can make this inspection more reliable and increase its information content.

Another object of this invention is to provide a method of non-destructive quality inspection of materials, which can ensure prompt access to information on the quality of a material having great length by rapidly defining the number of defects, their shape, and arrangement throughout the length of the material.

One more object of this invention is to provide a method of non-destructive quality inspection of materials, which can be used for detailed quality testing by increasing the resolution of the black-and-white or color image.

Yet another object of the invention is to provide a method of non-destructive quality inspection of materials, which can make this inspection more reliable by setting the system of coordinates of the black-and-white or color image in univocal correspondence with that of the material being inspected.

A further object of the invention is to provide a method of non-destructive quality inspection of materials, which makes this inspection reliable and increases its information content by furnishing a capability for prompt and accurate determination of coordinates and length of a defect.

The primary object of this invention is also to provide a videomonitor realizing the method of non-destructive quality inspection of materials, which is capable of continuous and prompt quality control of materials having great length, and ensures high reliability and information content of inspection.

Another object of the invention is to provide a videomonitor having improved resolution of the black-and-white or color image of defects in the material being inspected and, consequently, a higher information content of quality inspection.

Yet another object of the invention is to provide a videomonitor capable of making quality inspection more reliable by setting the coordinate system of the portion of the tested material being inspected.

Still another object of the invention is to provide a videomonitor which makes it possible to determine the length of a defect, its location on the portion of the material being inspected in relation to the reference point, including extended portions.

A further object of the invention is to provide a videomonitor which makes it possible to separate in time the process of picking up information on the quality of the extended material and the process of analyzing this information in order to detect defects.

These and other objects of the invention are achieved in a method of non-destructive quality inspection which comprises the steps of placing at least one transmitter of information on the quality of the material in the immediate vicinity of the surface of the material being inspected, setting the transmitter and material in motion in relation to each other, sampling information on the material quality fed by the transmitter, entering this information to the memory synchronously with the cycles of data transmitter displacement in relation to the tested material, reading this information from the memory by cycles, and converting it into a black-and-white or color picture which is used to assess the quality of the material being inspected, the address of the memory to start the next reading cycle being assigned prior to the beginning of this cycle.

It becomes possible, therefore, to display on the videomonitor screen any portion of the black-and-white or color image, to change the frames of the image if the capacity of the memory permits storage of information whose content exceeds one frame. It also becomes possible to separate in time the process of picking up information on the quality of the material being inspected and the process of information displaying for visual monitoring.

The information content and reliability of the material quality inspection can be greatly improved in this manner.

Advisably, the address of the working memory location which is to start the reading cycle, while information is being converted into a black-and-white or color picture, should be the address of the memory location to which the last recording had been made.

It becomes possible to display a sliding image on the screen so that continuous quality control of extended materials, such as long welds, can be effected. The information content and promptness of quality inspection are thus improved.

Advisably, information recording to the working memory should be gated by a pulse and, when the duration of the sampling pulse changes, the sampling frequency of information signals should be changed.

It becomes possible to improve the resolution of the black-and-white or color picture, to determine the distance to the defect from the data transmitter during acoustic non-destructive inspection and, consequently, to increase the information content of inspection.

Advisably, the location of the data transmitter and the direction of its displacement should be recorded with respect to a reference point on the material being inspected so that univocal correspondence is established between the coordinate systems of the black-and-white or color image and the material being inspected.

It becomes possible to set a scale of the image, to eliminate distortion of the image in relation to the real picture of the material being inspected and, consequently, to make non-destructive inspection more thrustworthy.

Advantageously, a marker line should be provided on the image, whose coordinates should be determined in advance in accordance with the location of the data transmitter in relation to the reference point on the material being inspected, and this marker line should be moved along the black-and-white or color picture in order to determine the location and length of any portion of the material.

It becomes possible to accurately determine the place of a defect in the material being inspected and its length. The information content and reliability of quality inspection is significantly improved in this way.

These objects are also achieved by a videomonitor realizing the method of non-destructive quality inspection of materials, comprising a data transmitter mounted on a device for scanning said data transmitter in relation to the material being inspected and a display unit connected in series to said data transmitter, as well as a control unit connected in series to an address unit, said control unit and address unit being connected, respectively, to synchronization outputs of the data transmitter and scanning device and to inputs of the display unit which comprises, connected in series, an analog-digital converter coupled to the output of the data transmitter, a memory, a digital-analog converter, and a display, while the address unit comprises a series-connected chain including a recording counter whose inputs are connected, respectively, to the synchronization output of the scanning device and to the control unit, and a switching circuit whose output is connected to the address input of the memory, and a readout counter inserted between the output of the control unit and the switching circuit. According to the invention the video monitor, also comprises a memory address code rewrite unit inserted between the output of the recording counter and the second input of the readout counter, while the other input of the code rewrite unit is connected to the output of the control unit.

It becomes possible to preset a working memory address of each subsequent readout cycle prior to the beginning of this cycle, and, in particular, the address of the memory location to which the last recording had been made, which shifts the image of the display screen, the former image being replaced by incoming information, and thus obtain a sliding image. It becomes possible to make quality inspection of extended material continuous, thus contributing to the expansion of the information content of inspection and expediting the process of testing.

Advisably, the address unit should comprise an image element counter whose output is connected to the switching circuit, and the control unit should comprise a variable frequency pulse generator connected to the input of the picture element counter and to the analog-digital converter, a sampling pulse generator whose input is connected to the data transmitter and whose output is connected to the recording counter, to the reset input of the image element counter, to the control input of the switching circuit, and to the input of the working memory, and a synchronizing generator whose outputs are connected, respectively, to the readout counter, the rewrite unit, and the digital-analog converter.

It becomes possible to sample information entered to the working memory, to change the length of the sampling pulse and its arrival time, to change the sampling frequency, and thus increase the resolution of the black-and-white or color image in order to obtain information on the distance to the defect from the data transmitter by applying acoustic non-destructive test methods. The information content of quality inspection is increased in this way.

Possibly, the address unit should comprise a rewrite signal generator inserted between the synchronizing generator and the memory address code rewrite unit, while the recording counter should be reversible, two inputs thereof being connected, respectively, to the second and third inputs of the rewrite signal generator and to two synchronization outputs of the scanning device.

It becomes possible to establish a univocal correspondence between the coordinate systems of the inspected zone and its image on the display and thus improve the trustworthiness of quality inspection.

Advisably, the videomonitor should comprise an image coordinate display unit connected to the address unit and to the control unit.

It becomes possible to determine the location and length of defects in the material being inspected and, consequently, to expand the information content of quality inspection.

Advisably, the coordinate display unit should comprise a reversible counter of marker line coordinates, whose two inputs are connected, respectively, to outputs of the synchronizing generator, a comparison unit connected in series to the up-down counter and having its second input connected to the second output of the readout counter, two OR elements having some inputs connected, respectively, to the second and third outputs of the up-down counter of marker line coordinates and other inputs connected, respectively, to the second and third outputs of the reversible recording counter, a reversible frame counter whose inputs are connected to outputs of the first and second OR elements, and a digital display unit connected in series to the reversible frame counter and having the second input thereof connected to the output of the marker line coordinate reversible counter.

It becomes possible to define the location and length of a defect much more accurately and, consequently, improve the reliability and trustworthiness of the material quality inspection.

Advisably, the address unit of the videomonitor should additionally comprise two OR elements inserted between the synchronization outputs of the scanning device and two inputs of the reversible recording counter, respectively, the second inputs of the OR elements being connected to respective outputs of the synchronizing generator.

It becomes possible to display on the screen any part of the material being inspected, because information concerning this part had been recorded in the working memory while the data transmitter had been passing this part earlier. In this case, the amount of information stored in the working memory may exceed the capacity of one frame. The desired part of the image can be selected for display by shifting the image on the screen without using the scanning device.

Rapid readout of information on the quality of material can be realized even with such methods of non-destructive quality inspection where the operational time of the data transmitter is restricted. The shadow color picture of the material being inspected can be analyzed afterwards, making the quality inspection still more reliable.

BRIEF DESCRIPTION OF ACCOMPANYING DRAWINGS

The invention will now be described in greater detail with reference to specific embodiments thereof and the accompanying drawings, wherein:

FIG. 5 shows a general block diagram of a videomonitor, according to the invention;

FIG. 6 shows a block diagram of a videomonitor realizing the method of non-destructive quality inspection of materials, according to the invention;

DESCRIPTION OF THE PREFERRED EMBODIMENTS

Figure 1:
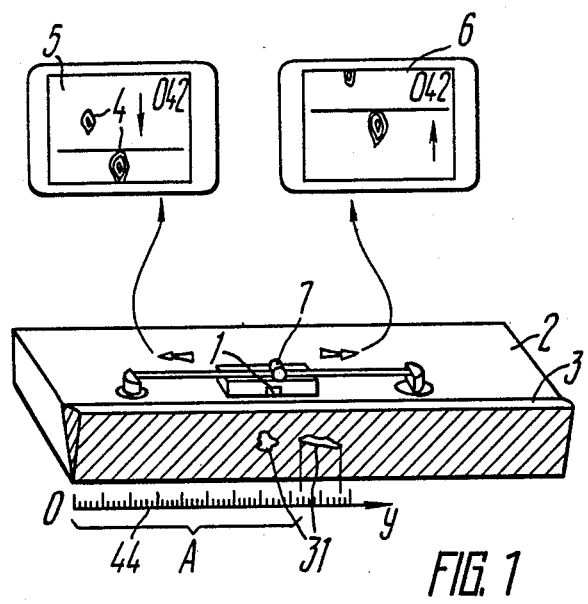
FIG. 1 shows a general diagram of a method of non-destructive quality inspection of materials, according to the invention.
Figure 2A:
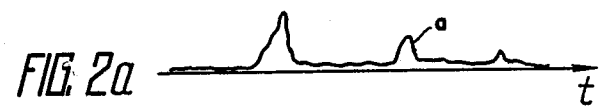
FIGS. 2A-2E show time diagrams of the information signal, gating pulse, and sequences of sampling pulses, according to the invention.
Figure 2B:
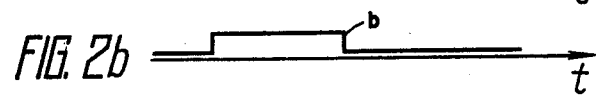
Figure 2C:
Figure 2D:
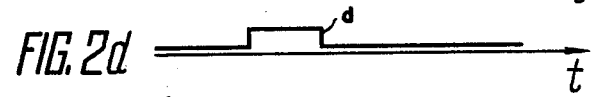
Figure 2E:

It should be pointed out at the outset that the claimed method of non-destructive quality inspection of materials may be an ultrasonic, magnetic-tape, or electromagnetic method. The data transmitter, accordingly, may comprise an ultrasonic transducer, or a magnetosensitive transducer, or an eddy-current transducer, or any other transducer depending on the method employed.

For simplicity the method of non-destructive quality inspection described below will be referred to a specific type of material testing, namely ultrasonic inspection of welded joints.

The proposed method of non-destructive quality inspection of materials comprises the following operations or steps.

A signal is obtained containing information on the quality of the material being inspected. This signal is converted into a black-and-white or color image, which is referred to as "image" hereinafter. To this end, a data transmitter 1 (FIG. 1) is applied on a portion 2 of the material and they are set into relative motion. The source information signal received by the data transmitter 1, e.g. acoustic, magnetic, or any other signal, is converted into an electrical signal which is sampled and digitized. The sequence of digital codes thus obtained is converted into a signal containing information on the quality of the portion 2 of the material being inspected. This signal is stored and kept for a required period. To produce an image, this information is periodically read, put through a digital-to-analog converter to produce line and frame synchronization signals and a video signal required to obtain a black-and-white or color image.

A sliding image is produced when moving the data transmitter 1 a long distance in relation to the portion 2 of the material being inspected. Thus, it can be transported along an extended weld 3. When, for example, the data transmitter 1 is transported along the weld 3 to the left, the image 4 of the defect is shifted down on a screen 5. The direction of the shift is indicated by an arrow on the screen. When the data transmitter 1 is shifted to the right, the color image 4 of the defect is shifted upwards. In this manner continuous inspection of an extended weld 3 can be performed interactively, on a real time basis, when signals of the data transmitter 1 are immediately displayed on the screen.

To this end, readout cycles should be started from those information signals which had been obtained last from the data transmitter 1 in order to convert the stored information into a black-and-white or color image. The information content and promptness of testing can be improved in this way.

Direct quality testing may be impracticable during the movement of the data transmitter 1 in relation to the tested material because the operational time of the data transmitter 1 is restricted and the amount of information fed thereto is too large due to the great length of the tested portion 2. In this case quality inspection is separated into two stages. At first, information on the quality of the tested material is stored during the period when the data transmitter 1 is operational. When the data transmitter 1 completes its working cycle, stored information is read and converted into a black-and-white or color image. The sliding image can be obtained by artificially assigning a sequence of signals starting the readout cycles while these signals are being converted into a color shadow image. In this way any portion of the image can be selected and analyzed in detail. The reliability and information content of quality inspection is greatly improved in this manner.

The resolution of the image can be controlled, if required.

To this end, the signal "a" (FIG. 2) is gated by a pulse "b" and sampled with a specific frequency $f_1$ (cf., pulse sequence "c").

Figures 3, 4:
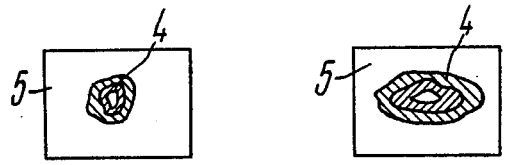
FIG. 3 shows a black-and-white or color image of a defect on the display screen, when the gating pulse duration is increased and the sampling frequency is reduced, according to the invention.
FIG. 4 shows an image of a defect on the display screen, when the duration of the gating pulse is increased and the sampling frequency is reduced, according to the invention.

The color shadow image 4 of the defect is obtained on the screen 5 (FIG. 3). Information on the defect is contained in the electrical signal a (FIG. 2) fed from the data transmitter 1. When the length of the gating pulse "d" becomes shorter, the sampling frequency $f_2$ (pulse sequence "e") should be increased to produce an image 4 (FIG. 4) of the defect, which has a higher resolution.

The next step is to establish a univocal correspondence between the coordinate systems of the tested material and the image 4 (FIG. 1).

To this end, a digital code 6 should be generated, which indicates a coordinate of an image part. Sync signals are produced as the data transmitter 1 covers a specific distance in relation to the tested material, this distance being constant throughout the path of the data transmitter 1. By counting the number of sync signals the distance covered by the data transmitter 1 can be determined in relation to some initial reference point. Further on, each sync signal indicative of a distance covered by the data transmitter 1 relative to the tested material is put into correspondence to a group of signals fed to storage from the data transmitter 1. Each group of information signals is, therefore, associated with a specific portion of the image on the screen 5 after the stored information if read and converted into a color shadow image. A reverse problem is to be solved, in other words, the image part of interest should be associated with a group of signals and, consequently, with the number of the sync signal in the sequence of these signals fed while the data transmitter 1 moves from the reference point. Then the distance from the portion 2 of the tested material, which corresponds to the selected image part, to the reference point is determined and a digital code 6 of the image part is generated.

Moreover, when the direction of movement of the data transmitter 1 in relation to the portion 2 of the tested material is reversed, the image shift is inhibited until the data transmitter 1 reaches that portion 2 of the tested material, whose image is not displayed on the screen 5. This eliminates distortions of the image on the screen 5 and improves the information content of reliability of testing.

The method of non-destructive quality inspection will be dealt with in more detail below when operation of the videomonitor realizing this method is described for a specific application—testing of welds.

An embodiment (FIG. 6) of a videomonitor realizing the method of non-destructive quality inspection of materials comprises a data transmitter 1 installed on a device 7 for scanning this transmitter 1 in relation to the portion 2 of the inspected material and connected in series with a display unit 8. The videomonitor also comprises, connected in series, a control unit 9 coupled to a synchronization output of the data transmitter 1 and to the display unit 8, and an address unit 10 connected to a synchronization output of the scanning device 7 and to the input of the display unit 5.

The display unit 8 may comprise an analog-digital converter 11 coupled to the data transmitter 1, a memory 12, a digital-analog converter 13, and a display 14, all these units being connected in series. The above mentioned units are well known to those skilled in the art and are used here for their primary purpose.

The display 14 may be a conventional black-and-white or color TV set. The address unit 10 may comprise series-connected units: a recording counter 15 connected to the synchronization output of the scanning device 7 and to the control unit 9, and a switching circuit 16 whose output is connected to the address input of the memory 12. The address unit 10 may also comprise a readout counter 17 inserted between the output of the control unit 9 and a respective input of the switch 16. According to the invention, an address code rewrite unit 18 inserted between the output of the recording counter 15 and the second input of the readout counter 17. The outputs of the control unit 9 are connected, respectively, to the analog-digital converter 11, the memory 12, the digital-analog converter 13, and to control inputs of the rewrite unit 18 and the switch 16.

The address code rewrite unit 18 is a conventional circuit connecting the information output of the recording counter 15 to the setting input of the readout counter 17, which provides a capability for controlling rewriting of information. The control unit 9 performs, in this case, the function of generating vertical and horizontal scan signals for the CRT display 14, synchronizing the operation of all units, and controlling recording and readout of information kept in the memory. Such units are commonly used in conventional TV games and raster displays. It is usually manufactured as a display controller. All other units of the videomonitor are conventional and, therefore, well known to those skilled in the art.

The rewrite unit 18 provides the videomonitor with a capability to form a sliding image, which substantially expands the information content of the device. The address unit 10 (FIG. 7) of the videomonitor may, according to the invention, comprise an image element counter 19 connected to a respective input of the switch 16. The control unit 9 may comprise a gating pulse generator 20 connected to control inputs of the image element counter 19, the switch 16, and the working storage 12, the input of the gating pulse generator 20 being connected to the synchronization output of the data transmitter 1. Besides, the control unit 9 may comprise a variable frequency pulse generator 21 connected to the input of the image element counter 19 and to the timing input of the analog-digital converter 11, and a synchronizing generator 22 whose outputs are connected, respectively, to the rewrite unit 18, to the readout counter 17, and to the digital-analog converter 13. In this case, the input of the recording counter 15 is connected to the synchronization output of the scanning device 7. All these units are well known to those skilled in the art. They are included in the device in order to provide a capability to control the resolution of the videomonitor, increasing or decreasing it as the case might be. The videomonitor is also capable of promptly determing the depth of defects or their position in relation to the weld limits, thus improving the information content of testing.

An image coordinate display unit 23 (FIG. 8) is provided, according to the invention, in the videomonitor in order to establish a univocal correspondence between the coordinate systems of the image and a specific portion of the tested material and, also, to precisely determine the position of any portion of the image in relation to the reference point and the length thereof. The image coordinate display unit 23 is connected to outputs of the control unit 9 and the address unit 10 and to the input of the display unit 8. Besides, the address unit 10 may comprise a rewrite signal generator 24 and the address code rewrite unit 18. The recording counter 15 may be reversible, two inputs thereof being connected, respectively, to two inputs of the rewrite signal generator 24 and to two synchronization outputs of the scanning device 7. The address unit 10 designed as described above can form a sliding image in two directions which correspond to the forward or reverse movement of the data transmitter 1 effected by the scanning device 7.

The address unit 10 can also eliminate distortions of the image when the direction of the data transmitter 1 is reversed, thus improving the trustworthiness of testing.

The rewrite signal generator 24 is a conventional logic circuit built around known logic elements. A specific embodiment of such circuit is described below.

The image coordinate display unit 23 may comprise a reversible counter 25 of marker line coordinates, whose two inputs are connected, respectively, to outputs of the synchronizing generator 22 and which is coupled in series to a comparison circuit 26 whose second input is connected to the second output of the readout counter 17; a first and a second OR elements 27 and 28 whose first inputs are connected, respectively, to the second and third outputs of the marker line coordinate reversible counter 25, while the second inputs thereof are connected, respectively, to the third and fourth outputs (carry and borrow outputs) of the reversible recording counter 15. In addition, the image coordinate display unit 23 comprises a reversible counter 29 of image frames, whose inputs are connected to outputs of the first and second OR elements 27 and 28 and which is coupled in series to a digital indication unit 30 whose second input is connected to the output of the marker line coordinate reversible counter 25. This electrical connection of units in the image coordinate display unit 23 permits a substantial increase in the information content of the quality inspection. It becomes possible to precisely determine the position of length of defects 31 in the material 2 (FIG. 1) being inspected. The above mentioned units are known to all those skilled in the art.

Besides, the address unit 10 of the videomonitor may, according to the invention, comprise two OR elements 32 and 33 inserted between the synchronization outputs of the scanning device 7 and two inputs of the reversible recording counter 15, respectively. The second inputs of the third and fourth OR elements 32 and 33 are connected to respective outputs of the synchronizing generator 22. This arrangement of the address unit 10 permits prompt testing and increases the information content of tests. This is particularly true for non-destructive methods where information on the inspected material is to be picked up expeditiously.

Figure 10:
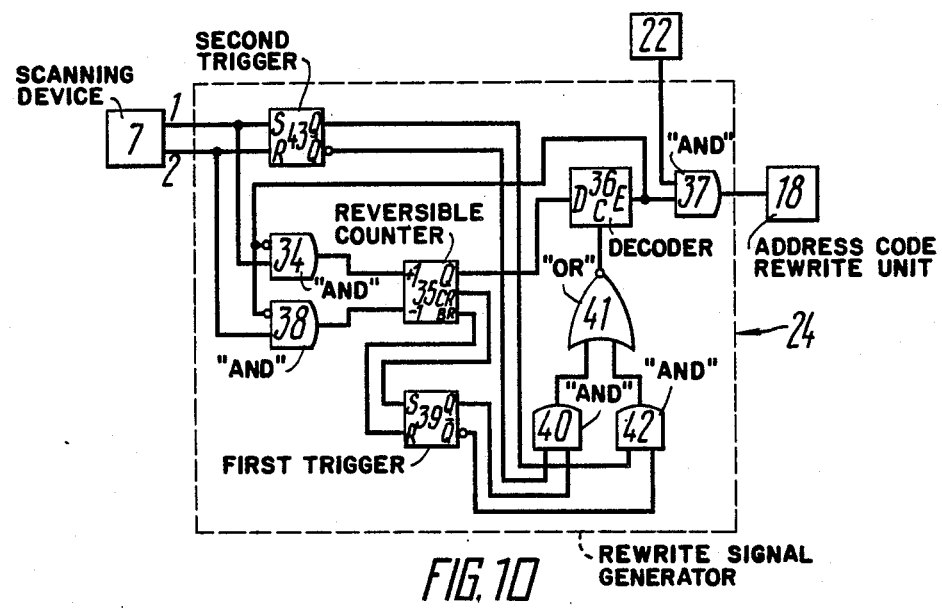
FIG. 10 shows a block diagram of a rewrite signal generator, according to the invention.

An embodiment of the rewrite signal generator 24 is shown in FIG. 10.

The rewrite signal generator 24 comprises a series-connected chain including a first AND element 34 whose input is connected to the first synchronization output of the scanning device 7, a reversible counter 35, a decoder 36, and a second AND element 37; a third AND element 38 whose input is connected to the second synchronization output of the scanning device 7, while the output thereof is connected to the second input of the reversible counter 35, a series-connected chain including a first trigger 39 whose two inputs are connected to two respective outputs of the reversible counter 35, a fourth AND element 40, and an OR element 41 whose output is connected to the gating input of the decoder 36, a fifth AND element 42 whose input is connected to the second output of the first trigger 39, while the output thereof is connected to the second input of the OR element 41, and a second trigger 43 whose two setting inputs are connected, respectively, to the first and second outputs of the scanning device 7, while the inverting and non-inverting outputs are connected, respectively, to the second inputs of the fourth and fifth AND elements 40 and 42.

The second input of the second AND element 37 and the output thereof are connected, respectively, to the output of the synchronizing generator 22 and to the control input of the address code rewrite unit 18.

The videomonitor realizing the new method of nondestructive quality inspection of materials operates, according to the invention, as follows.

The data transmitter 1 (FIG. 1) mounted on the scanning device 7 is transported along the portion 2 of the material being inspected, specifically along the weld 3. The analog signal produced by the data transmitter 1 (FIG. 6) is converted in the analog-digital converter 11 into a digital code and supplied to the memory 12. Using the signal fed from the synchronization output of the scanning device 7 and timing signals fed from the output of the control unit 9, the recording counter 15 forming the code of the memory address location whereto the recording is made.

A signal of the control unit 9 makes the switch 16 disconnect the outputs of the readout counter and connects the outputs of the recording counter to the address inputs of the memory. The control unit 9 generates a recording instruction fed to the memory 12. In this manner, the incoming information is recorded into the memory 12. During readout and display, the control unit 9 uses the switch 16 to supply the address of the storage location to be read to the address inputs of the memory 12. Then the control unit 9 generates a signal for the digital-analog converter 13 which converts the digital code into an analog signal fed to the display 14 where it is transformed into a color shadow image.

The complete counting cycle of the counters 15 and 17 is sufficient to address all memory locations in the memory 12, which corresponds to full recording and readout cycles.

In this particular example explaining the operation of the device the recording counter 15 is assumed to count down and goes through the states $n, n-1, \ldots, n+1$ during the complete counting cycle, while the counter 17 counts forward and goes through the states $n, n+1, \ldots, n-1$. The readout counter 17 completes one full counting cycle within a period required for displaying one field on the screen 5 of the display 15. This means that a complete frame is displayed on the screen 5 during two full cycles of the readout counter 17.

A signal enabling rewriting of the current code of a storage address from the outputs of the recording counter 15 to the readout counter 17 is supplied from the control unit 9 to the address code rewrite unit 18 at the end of every other counting cycle of the counter 17. This means that at the beginning of every other counting cycle the output of the readout counter 17 is the code of the storage address to which the last recording had been made, and, consequently, each new frame displays new information. Since the recording counter 15 counts down, the address code of the memory location which starts the display of a frame coincides with or precedes the address code of the memory location which started the display of the preceding frame. In consequence, the image on the videomonitor screen is successively shifted and replaced by new information fed from the data transmitter transported along the material 2. In this manner a sliding image is produced. This offers the advantage of continuous quality inspection of an extended material, particularly a long weld 3, on a real time basis.

Figure 7:
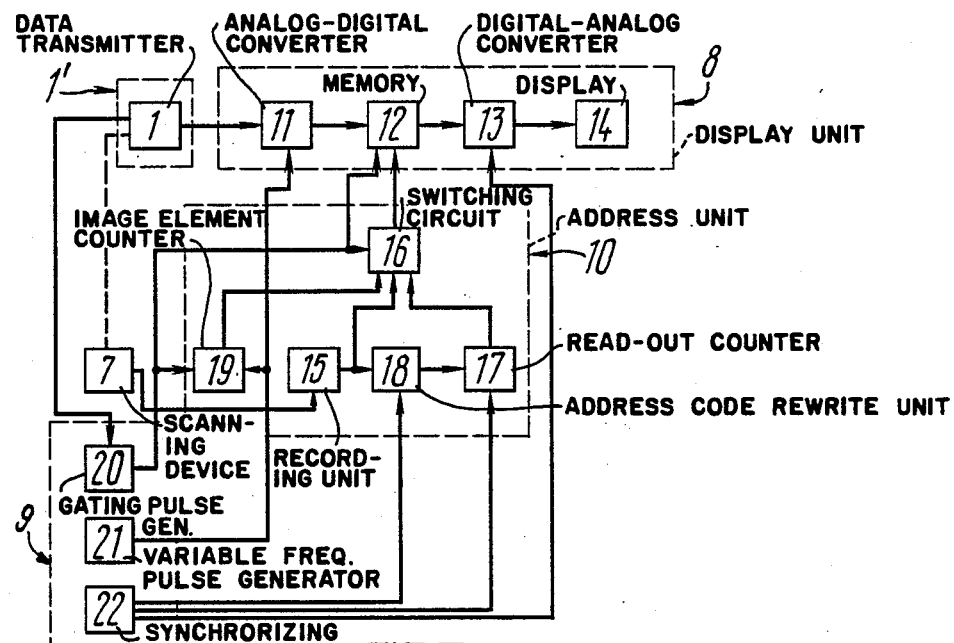
FIG. 7 shows a block diagram of a videomonitor realizing an embodiment of the method of non-destructive quality inspection of materials, according to the invention.

The block diagram of FIG. 7 shows the videomonitor which, in addition to the above positive effect, also offers the advantage of changing the resolution of the image. The gating pulse generator 20 is activated by pulses fed from the data transmitter 1. The duration and position of the gating pulse which is the output pulse of the generator 20 can be varied in order to make the gating pulse coincide in time with the information signal or an arbitrary portion of this signal applied to the input of the analog-digital converter 11.

The gating pulse is supplied to the control input of the memory 12 and sets it to the recording mode. The gating pulse is supplied to the switch 16 and sets it to the position in which the address code fed from the outputs of the recording counter 15 and the image element counter 19 is supplied to the address inputs of the working storage 12. Information fed from the output of the analog-digital converter 11 to the memory 12 is recorded in the memory location having this address. Timing pulses whose frequency can be adjusted are supplied from the output of the variable frequency pulse generator 21 to the counting input of the image element counter 19. The frequency of timing pulses is selected so that the length of the gating pulse is equal to $2^n - 1$ periods of timing pulses, where n is the number of digits of the image element counter 19.

In this manner signals are sampled and recorded, each signal being represented as a sequence of digital codes in the memory 12 which is a table memory. The number of a line in the table is provided by the recording counter 15, while the number of the memory location in the line is provided by the image element counter 19. The number of memory locations in a line is equal to $2^n - 1$.

With no gating pulse applied, the image element counter 19 is reset and the memory 12 starts the readout, the outputs of the readout counter 17 being connected via the switch 16 to the address inputs of the memory 12. The readout counter 17 interrogates all memory locations and the lower-order digits produce the code of the memory location in a line, while the higher order digits produce the line number code. During the readout information is displayed on the screen 5 of the display 14 line by line. Signals are converted into colored or black-and-white stripes and their totality forms a colored or black-and-white image of the portion of the material being inspected.

When the gating pulse becomes longer, the duration $2^n - 1$ of the timing pulse periods becomes less than the length of this gating pulse. In this case some information is lost since the image element counter 19 starts a new counting cycle when it completes the former one. As a result, some elements of information recorded in the memory 12 are erased. In order to avoid the distortion, the frequency of timing pulses has to be decreased by shortening the output pulses of the variable frequency pulse generator 21.

When the gating pulse decreases, the duration $2^n - 1$ of timing pulse periods becomes longer than the length of the gating pulse. In this case, each memory line is supplied with less information than it is capable of accomodating and, consequently, the remaining memory locations retain former information which is the cause of distortions during readout. In order to eliminate the distortion, the frequency of timing pulses will have to be increased.

Shorter gating pulses and respective adjustment of the frequency of timing pulses permit control of sufficiently short portions of the information signal and higher resolution of the image. Higher resolution of the videomonitor means greater information content can be displayed thereon.

The frequency of the variable frequency pulse generator 21 may be adjusted by any known methods in order to change the length of the gating pulse.

Referring to FIG. 2, the time charts show information signal "a", the gating pulse "b", the timing pulse sequence "c" having the frequency $f_1$, the gating pulse "d" which is half as long as the gating pulse "b", the timing pulse sequence "c" whose frequency $f_2$ is twice as high as the frequency $f_1$.

FIG. 3 shows a colored shadow image of a portion of the material being inspected when the information signal "a" is gated by the pulse "b" and timed by the sequence of pulses "c" with the frequency $f_1$.

FIG. 4 shows a colored shadow image of a portion of the material being inspected when the information signal "a" is gated by the gating pulse "d" and timed by the sequence of pulses "c".

Comparison of the images of FIGS. 3 and 4 demonstrates that the resolution of the image in FIG. 4 is twice as high as that of FIG. 3.

It can also be demonstrated that by changing the position of the gating signal in time the position of the image 4 of the defect changes in relation to the boundaries of the screen 5. Thus, for example, when the gating pulse is shifted to the right on the time axis of the chart shown in FIG. 2, the respective image on the screen 5 (FIGS. 3 or 4) moves down and, when the gating pulse is shifted to the left, the image on the screen 5 moves to the right.

This offers a new advantage when using acoustic non-destructive testing techniques. The depth of a defect can be determined during vertical sounding by watching the position of the image 4 of this defect on the screen 5 or the position of the defect in relation to the boundaries of the weld 3 (FIG. 1). For this purpose, several parameters have to be set in advance, such as the length of the gating pulse, its position in time, and the frequency of sampling of the generator 21.

The above described operations permit a substantial increase in the information content of testing.

Figure 8:
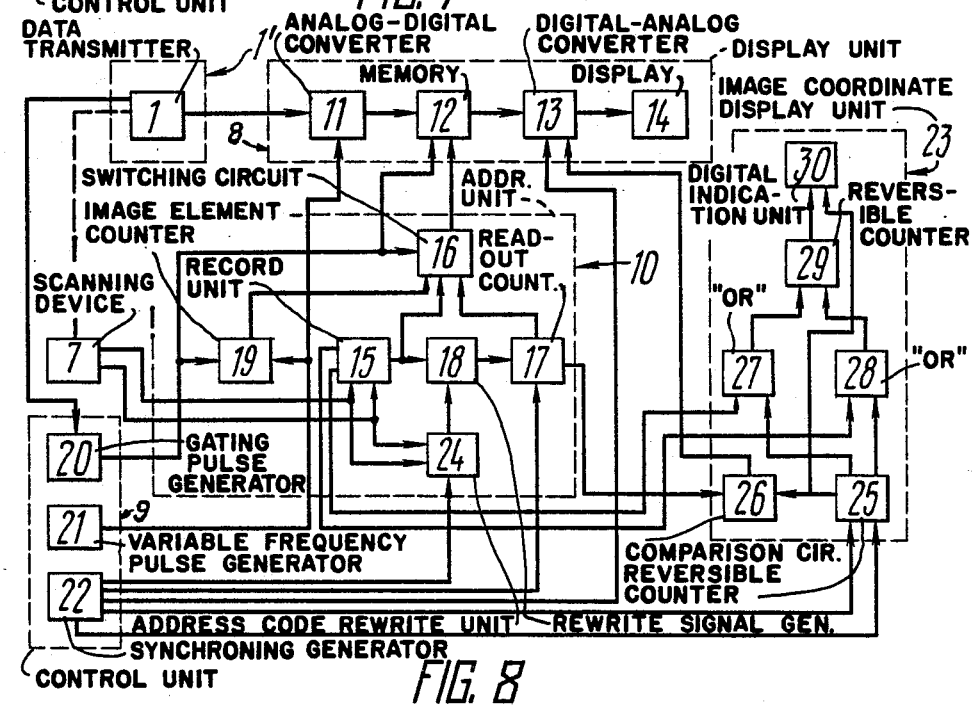
FIG. 8 shows a block diagram of a videomonitor realizing another embodiment of the method of non-destructive quality inspection of materials, according to the inspection.

FIG. 8 shows a block diagram of a videomonitor which, in addition to the above described positive effect, offers the advantage of higher reliability and greater information content of testing.

In this embodiment, the recording counter 15 is reversible and the scanning device 7 can produce, in addition to synchronization signals, a signal indicating the direction of movement of the data transmitter 1 in relation to the material 2 being inspected.

At first, the system of coordinates of the portion of the material to be inspected is entered. In the example of FIG. 1 this is the axis OY extending along the weld 3 with a scale rule 44 marked thereon.

The system of coordinates of the image is the axis OY' arranged, in this case, in the plane of the videomonitor screen.

The coordinate axis OY of the material portion being inspected can be divided into sections each having "m" equal portions. In this case, the number "m" is equal to the number of lines in the working storage 12 and, consequently, to the number of lines of the image, which are the structural components of the image.

It is clear from the foregoing that each number of a line of the memory locations in the memory 12 corresponds to the number of a line of the image on the screen 5. When the scanning device 7 passes each said portion, a synchronization signal is produced at the output thereof and supplied to the counting input of the reversible counter 15 and changes its state. When the scanning device 7 passes a section having "m" equal portions, "m" synchronization signals are taken from the output thereof and the reversible recording counter 15 completes a full counting cycle. Addresses are assigned to all lines of memory locations in the memory 12, which correspond to all lines of image elements in one frame of the image 4.

When the scanning device 7 moves in the positive direction in relation to the OY axis (to the right in FIG. 1), the reversible recording counter 15 counts forward and the image on the screen 5 moves up. When the scanning device moves in the opposite direction, the image on the screen 5 is shifted down. This means that the positive direction of the OY axis on the tested material corresponds to the positive direction of the OY' axis of coordinates of the colored shadow image on the screen 5.

The image element counter 19 is responsible for recording information to the memory locations of each line. Since a memory location can be filled only when a sync pulse is supplied by the scanning device 7 and each line of memory locations corresponds to the image line on the screen 5, each section of the path of the scanning device 7 can be assigned to a specific portion of the OY' axis, which is equal to the width of the image line.

The reversible counter 25 of the marker line coordinates and the comparison unit 26 are used to form a marker line which is used to indicate any image element on the screen 5 (FIG. 1). By feeding pulses from the synchronizing generator 22 to the up or down input of the reversible counter 25 of the marker line coordinates, any code ranging from 0 to $m-1$ can be obtained at the output of the reversible counter 25, where "m" is the number of image element lines on the screen 5. The binary code from the output of the reversible counter 25 of the marker line coordinates is supplied to the input of the unit 30 for digital indication of coordinates and to the input of the comparison unit where it is compared with the binary code fed from the higher-order digits of the readout counter 17. At the moment of comparison of the two codes, a signal is supplied to the input of the digital-analog converter 13 to produce an image of the marker line on the screen 5.

In this manner a marker line is produced on the colored shadow image in the line whose number is assigned by the reversible counter 25 of the marker line coordinates. The coordinate of the marker line is displayed on the digital display of the digital indication unit 30 as referred to the system of coordinates of the image.

Since each coordinate on the OY' axis is associated with a specific section of the path along the OY axis on the tested material, the length of any image portion on the screen 5 can be determined by shifting the marker line along the axis OY' of the image in order to determine the length of a respective portion of the tested material.

This offers the advantage of improved accuracy of measurements of the length of defects in the portion 2 of the tested material. It also makes testing more reliable and increases its information content.

If the zero coordinate of the marker line is set when the scanning device 7 is in the initial position (the reference point), the distance from this reference point to any portion of the inspected material, whose image on the screen 5 is indicated by the marker line, can be easily determined as the scanning device 7 is transported along the material.

The reversible counter 29 of image frames is provided in the videomonitor in order to expand the range of the coordinate system of the image.

The carry signal is supplied from the output of the reversible counter 25 of the marker line coordinates to the input of the first OR element 27 and, further on, from the output of the OR element 27 to the up input of the reversible counter 29 of image frames and sets it to a higher level. The binary code is further supplied from the output of the reversible counter 29 of image frames to the second input of the digital indication unit 30 where the coordinate of the image is displayed as the frame number. The borrow signal is supplied from the output of the reversible counter 25 of the marker line coordinate to the input of the second OR element 28 and, from the output thereof, to the down input of the reversible counter 29 of image frames, setting it to a lower level. Carry and borrow signals from the outputs of the reversible recording counter are supplied to the second inputs of the OR elements 27 and 28 and, from the outputs thereof, to the up or down inputs of the reversible image frame counter 29 setting it to a higher or lower level.

No matter how long is the path of the scanning device 7 along the weld 3, the coordinate of any portion of this weld 3 can be determined as the number of an image frame, since the length of the frame, as has been described above, corresponds to the sum of "m" sections along the OY axis and as a coordinate of the marker line.

The rewrite signal generator 24 whose block diagram is shown in FIG. 10 is intended to eliminate image distortions when the direction of the movement of the scanning device 7 is reversed. When the scanning device 7 (FIG. 1) moves in the positive direction, the image on the screen 5 moves down. This means that new information is displayed in the lower part of the screen pushing the old information upwards out of the frame. When the scanning device 7 moves in the negative direction, the image moves downward.

To keep new information within the frame (when it is pushed out, it appears at the opposite end of the screen) during the reversal of the direction of movement of the scanning device 7 and maintain an undistorted image, it is necessary to temporarily discontinue the image shift, that is to inhibit the operation of the address code rewrite unit 18 until information fed after the direction reversal fills all "m" lines of the image. This function is performed by the rewrite signal generator 24.

The rewrite signal generator 24 operates as follows.

When the scanning device 7 (FIG. 1) moves in the positive direction in relation to the OY coordinate axis, sync pulses are supplied from the first output thereof to the first input of the first AND element 34 (FIG. 10) and to the set input of the second trigger 43. No signals are supplied in this case from the second synchronization output of the scanning device 7. When the scanning device 7 moves in the negative direction the processes are reversed. The reversible counter 35 counts forward when pulses from the output of the first AND element 34 are applied to the first input of the counter 35. This is possible when an enable signal is supplied from the output of the decoder 36 to the second input of the first AND element 34 and the scanning device moves in the positive direction.

The output signal of the decoder 36 is enabling for the first and third AND elements 34 and 38 and prohibiting for the second AND element 37, and visa versa.

The decoder 36 detects the zero state of the reversible counter 35 and, if an active signal level is available at the gating input thereof, generates the enabling signal applied to the first input of the second AND element 37 and, consequently, inhibiting signals for the first and third AND elements 34 and 38.

Initially, the two triggers 39 and 43 and the reversible counter 35 are in the zero state. No active level signal is supplied from the outputs of the fourth and fifth AND elements 40 and 42 to the inputs of the OR element 41. The active level signal is therefore supplied from the output of the OR element 41 to the gating input of the decoder 36.

When the scanning device 7 moves in the positive direction, the very first signal fed from the synchronizing output thereof sets the trigger 43. As a result, the active signal level appears at the gating input of the decoder 36, and an enabling potential is applied to the second input of the first AND element 34.

No rewrite signal is produced at the output of the second AND element 37 since an inhibiting signal is applied to the first input thereof. This means that at this stage of movement of the scanning device 7 the image 4 on the screen 5 is not shifted.

A sync pulse supplied from the first output of the scanning device 7 via the first AND element 34 to the up input of the reversible counter 35 sets this counter 35 to a state other than zero and thus confirms the inhibiting signal at the input of the second AND element 37. The scaling factor of the reversible counter 35 is equal to "m" which is the number of lines of an image in a frame. The carry signal fed from the output of the reversible counter 39 sets the trigger 39 and an active signal level again appears at the gating input of the decoder 36. Since zero code is set at the output of the reversible counter 35, the output of the decoder 36 is a potential applied to the input of the first AND element 34. The operation of this AND element 34 is thus inhibited and, consequently, no pulses are fed to the input of the reversible counter 35 which retains its former state.

An enabling potential being applied to the input of the second AND element 37, timing pulses fed from the output of the synchronizing generator 22 produce, at the output thereof, rewrite signals supplied to the control input of the address code rewrite unit 18. The image 4 on the screen 5 is shifted in the positive direction with respect to the OY' axis. This goes on until the scanning device 7 moves in the positive direction with respect to the OY axis.

When the direction of movement of the scanning device 7 is reversed, shift synchronizing pulses are generated at the second output thereof. The very first sync pulse resets the trigger 43 and, consequently, an active signal level is set at the output of the fourth AND element 40 while it is removed from the gating input of the decoder 36. An enabling potential is supplied to the second input of the third AND element 38 and pulses start arriving to the down input of the reversible counter 35. Since this reversible counter 35 had been in the zero state, the first pulse applied to the down input thereof generates a borrow signal at the output of the counter 35, which resets the trigger 39. An active signal level is restored at the gating input of the decoder 36. But since the binary code at the output of the reversible counter 35 had changed and is not zero, the output of the decoder 36 is restored to become a signal level active for the third AND element, which inhibits the operation of the second AND element 37. The shift of the image 4 on the screen 5 is discontinued, and the reversible counter 35 starts counting sync pulses fed from the scanning device 7 until a zero binary code is set at the information output thereof. Since an active signal level is kept at the gating input of the reversible counter 35, the output of the decoder 36 is a signal enabling the operation of the second AND element 37 and inhibiting the operation of the third AND element 38. As a result, the reversible counter 35 stops counting and remains in the zero state, while the image 4 on the screen 5 starts shifting in the negative direction with respect to the coordinate axis OY' as the scanning device 7 moves in the negative direction in relation to the axis OY.

This offers the advantage of making the quality inspection more reliable.

Figure 9:
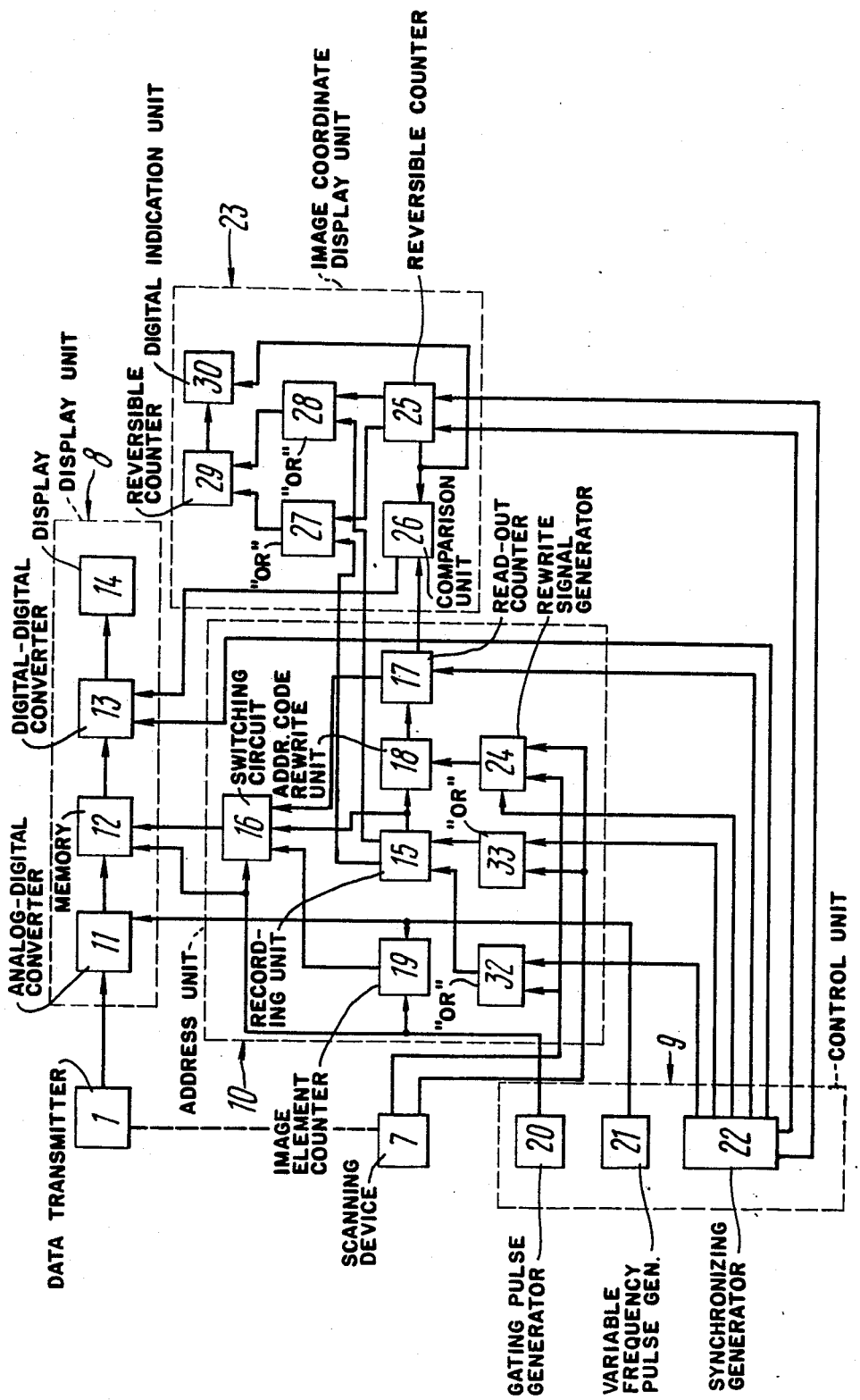
FIG. 9 shows a block diagram of a videomonitor having a larger working memory, according to the invention.

To separate in time the processes of recording data in the memory 12 and analyzing these data by visual inspection, the videomonitor of FIG. 9 is provided with the third and fourth more OR elements 32 and 33. They permit feeding signals to the up and down inputs of the reversible recording counter 15 both from the synchronizing outputs of the scanning device 7 and from the outputs of the synchronizing generator 22. When signals are supplied from the synchronizing generator 22, the gating pulse generator 20 is disabled and the memory 12 starts reading. The codes of memory location addresses from which readout cycles are started are generated by the reversible recording counter 15. They are rewritten, after each readout cycle, to the readout counter 17. A colored or black-and-white image kept in the memory 12 can thus be recalled, the capacity of the memory 12 being in excess of the information volume required to display one frame on the screen 5. In this case, the number of states of the counters participating in the entering information to the memory 12 and its readout should correspond to the number of memory locations of the memory 12. The readout counter 17 should pass, during readout cycles, the number of states which corresponds to the number of memory locations required to obtain a complete frame of colored or black-and-white image.

This offers the advantage of making the quality inspection more reliable, thrustworthy, and rapid.

The new method for non-destructive quality inspection of materials and a videomonitor realizing this method have a very broad field of application. They can be used in gas and oil extracting industry—for pipe weld quality testing, in machine building industry—for detecting defects in rolled products, in ship-building industry—for testing the quality of welds of ship hulls and tanks, and in other fields where non-destructive quality inspection of materials is readily applicable.

In addition, the proposed method and device can be used in medicine.

The proposed invention can be used for many purposes. It can be easily adapted for various methods of non-destructive testing, such as ultrasonic, magnetographic, heat, etc. The use of the new method is a positive contribution which can make quality inspection more reliable and thrusworthy, increase its information content, and, at the same time, make the work of operators engaged in this process more efficient.

This invention is most profitable when used to test extended objects or when the time for readout of information on the quality of the tested material is strictly limited.

The invention's primary object is to reveal the state of the tested material, but it can also be used to locate the position and determine the length of any portion of the tested material, whose quality deviates from a standard. It can be used for detailed analysis of some portions of the tested material by adjusting the resolution of the image on the proposed videomonitor.

What is claimed is:

1. A method of non-destructive quality inspection of materials, comprising the steps of:
    placing at least one transmitter of data on the quality of a material in the immediate vicinity of the surface of said material to be inspected;
    setting said data transmitter and said inspected material in motion relative to each other;
    setting a minimal distance to which said data transmitter is displaced in relation to the inspected material, which is taken as a displacement cycle;
    sampling information fed by said data transmitter;
    entering obtained information to a memory synchronously with said displacement cycles of said data transmitter in relation to said inspected material;
    periodically reading this information contained in said memory and, prior to the beginning of each next readout cycle, assigning an address of a location in said memory, from which this readout cycle is to start;
    converting information read out in this manner into a colored or black-and-white shadow image indicative of the quality of the inspected material, wherein recording of information to said memory is gated by a pulse whose duration corresponds to the frequency of said sampling of information signals and, when the duration of said gating pulse changes, the frequency of sampling of information signals is also changed.

2. A method of non-destructive quality inspection of materials, comprising the steps of:
    placing at least one transmitter of data on the quality of a material in the immediate vicinity of the surface of said material to be inspected;
    setting said data transmitter and said inspected material in motion relative to each other;
    setting a minimal distance to which said data transmitter is displaced in relation to the inspected material, which is taken as a displacement cycle;
    sampling information fed by said data transmitter;
    entering obtained information to a memory synchronously with said displacement cycles of said data transmitter in relation to said inspected material;
    periodically reading this information contained in said memory and, prior to the beginning of each next readout cycle, assigning an address of a location in said memory, from which this readout cycle is to start;
    converting information read out in this manner into a colored or black-and-white shadow image indicative of the quality of the inspected material, an arbitrary reference point being set on said material being inspected;
    determining the direction of displacement of said data transmitter and the position thereof in relation to said reference point;
    establishing a univocal correspondence between the system of coordinates of said image and the system of coordinates of the material being inspected.

3. A method as claimed in claim 2, in which
a marker line is formed in said system of coordinates of the colored or black-and-white image;
the coordinates of said marker line are set in accordance with the position of said data transmitter in said coordinate system of the material being inspected;
said marker line is displaced along said coordinate system of the image;
the position and length of a portion of the inspected material is determined in accordance with the position of said marker line within said system of coordinates of the colored or black-and-white image.

4. A method of non-destructive quality inspection of materials, comprising the steps of placing at least one transmitter of data on the quality of a material in the immediate vicinity of the surface of said material being inspected;
setting said data transmitter and said material being inspected in motion relative to each other;
setting a minimal distance to which said data transmitter is displaced in relation to the material being inspected, which is taken as a displacement cycle;
sampling information fed from said data transmitter;
recording the information thus obtained to a memory synchronously with said displacement cycles of said data transmitter relative to said inspected material;
gating recording of information in said memory by a pulse whose duration corresponds to the frequency of said sampling of information signals and, when the duration of said gating pulse changes, changing the frequency of sampling of information signals;
periodically reading the processed information contained in said memory and, prior to the beginning of each next readout cycle, assigning an address of a location in said memory, from which this readout cycle is to start;
converting information read out in this manner into a colored or black-and-white image indicative of the quality of said material being inspected;
setting an arbitrary reference point on said material being inspected;
determining the direction of displacement of said data transmitter and its position relative to said reference point;
establishing univocal correspondence between a system of coordinates of said image and a system of coordinates of said inspected material;
generating a marker line in said system of coordinates of the image;
setting the coordinates of said marker line in correspondence with the position of said data transmitter in said system of coordinates of the material being inspected;
shifting said marker line along said system of coordinates of the image;
determining the location and length of a portion of the inspected material in accordance with the position of said marker line in said system of coordinates of the image.

5. A videomonitor for non-destructive quality inspection of materials, comprising:
a scanning device for scanning relative to said inspected material, which is placed in the immediate vicinity of said inspected material;
a transmitter of data on the quality of the inspected material, installed on said scanning device;
a display unit comprising:
an analog-digital converter having at least two inputs and one output, one of said inputs being connected to an output of said transmitter of data on the quality of the inspected material;
a memory having at least three inputs and an output, one said input being connected to the output of said analog-digital converter;
a digital-analog converter having at least two inputs and an output, one said input being connected to the output of said memory;
a color display of the quality of said inspected material, whose input is connected to the output of said digital-analog converter;
an address unit comprising:
a recording counter having at least two inputs and an output, one said input being connected to the output of said scanning device;
a switch having at least three inputs and an output, one said input being connected to the output of said recording counter, while the output thereof is connected to said second input of said working storage;
an address code rewrite unit having at least two inputs and an output, one said input being connected to the output of said recording counter;
a readout counter having at least two inputs and an output, one said input being connected to the output of said address code rewrite unit, while the output thereof is connected to said second input of said switch;
a control unit having at least one input and seven outputs, one said input being connected to another output of said transmitter of data on the quality of the inspected material, said first output being connected to said second input of the analog-digital converter, said second output being connected to said third input of the memory, said third output being connected to said second input of the recording counter, said fourth output being connected to said second input of the address code rewrite unit, said fifth output being connected to said second input of the readout counter, said sixth output being connected to said third input of the switch, and said seventh output being connected to said second input of the digital-analog converter.

6. A videomonitor as claimed in claim 5, wherein said control unit comprises:
a gating pulse generator whose input is connected to said data transmitter, while the output thereof is connected to said third input of said switch and to said third input of said memory;
a variable frequency pulse generator having its output connected to said second input of the analog-digital converter;
a synchronizing generator having at least three outputs, said first output being connected to said second input of the digital-analog converter, said second input being connected to said second input of the readout counter, while said third output is connected to said second input of the address code rewrite unit;
said address unit additionally comprises:
an image element counter having at least two inputs and an output, said first input being connected to said output of the gating pulse generator, said second input being connected to said output of the variable frequency pulse generator, and said output being connected to a first additional input of said switch.

7. A video monitor as claimed in claim 5, wherein said control unit comprises:
  a gating pulse generator having its input connected to said data transmitter and having its output connected to said third input of said switch and to said third input of said memory;
  a variable frequency pulse generator having its output connected to said second input of said analog-digital converter;
  a synchronizing generator having at least three outputs, said first output being connected to said second input of the digital-analog converter, said second input of the digital-analog converter, said second output being connected to said second input of the readout counter;
said address unit additionally comprises:
  an image element counter having at least two inputs and an output, said first input being connected to said output of the gating pulse generator, said second input being connected to said output of the variable frequency pulse generator, while said output is connected to a first additional input of said switch;
  a rewrite signal generator having at least three inputs and an output, said first input being connected to said third output of said synchronizing generator, and said output being connected to said second input of said address code rewrite unit;
  a reversible recording counter having at least two inputs and an output, said first input being connected to said second input of said rewrite signal generator and to an output of said scanning device, said second input thereof being connected to said third input of said rewrite signal generator and to another output of said scanning device, and said output thereof being connected to said first input of the switch.

8. A videomonitor as claimed in claim 6, comprising an image coordinate display unit comprising:
  a reversible counter of coordinate of said marker line, which has at least two inputs and three outputs, said first input thereof being connected to the first additional output of said synchronizing generator, and said second input being connected to the second additional output of said synchronizing generator;
  a comparison unit having at least two inputs and an output, said first input being connected to said first output of said marker line coordinate reversible counter, said second input being connected to the first additional output of said readout counter, and said output being connected to the first additional input of said digital-analog converter;
  a first OR element having at least two inputs and an output, said first input being connected to said second output of said marker line coordinate reversible counter, and said second input being connected to the first additional output of said reversible recording counter;
  a second OR element having at least two inputs and an output, said first input being connected to said third output of the marker line coordinate reversible counter, and said second input being connected to the second additional output of said reversible recording counter;
  an image frame reversible counter having at least two inputs and an output, said first input being connected to said output of said first OR element, and said second input being connected to said output of said second OR element;
  a digital indication unit having at least two inputs, said first input being connected to said output of said image frame reversible counter, and said second input being connected to said first output of said marker line coordinate reversible counter.

9. A videomonitor as claimed in claim 7, wherein said address unit additionally comprises:
  a third OR element having at least two inputs and an output, said first input being connected to an output of said synchronizing generator, said second input being connected to an output of said scanning device, and said output being connected to said first input of said recording reversible counter;
  a fourth OR element having at least two inputs and an output, said first input being connected to an output of the synchronizing generator, said second input being connected to another output of said scanning device, and said output being connected to said second input of said recording reversible counter.

10. A videomonitor for non-destructive quality inspection of materials, comprising:
  a scanning device for scanning in relation to said material being inspected, which is installed in the immediate vicinity of said inspected material;
  a transmitter of data on the quality of the inspected material, which is mounted on said scanning device;
  a display unit having:
  an analog-digital converter having at least two inputs and an output, one said input being connected to an output of said transmitter of data on the quality of said material being inspected;
  a memory having at least three inputs and an output, one said input being connected to said output of the analog-digital converter;
  a digital-analog converter having at least three inputs and an output, one said input being connected to the output of said memory;
  a black-and-white or color display of the quality of said material being inspected, having an input connected to the output of said memory;
  a control unit having:
  a gating pulse generator having at least one input and one output, said input being connected to the input of said data transmitter, and said output being connected to said second input of said memory;
  a variable frequency pulse generator having an output connected to said second input of said analog-digital converter;
  a synchronizing generator having at least seven outputs, said first output being connected to said second input of the digital-analog converter;
  an image coordinate display unit having:
  a marker line coordinate reversible counter having at least two inputs and three outputs, said first input being connected to said second output of the synchronizing generator, and said second input being connected to said third output of the synchronizing generator;
  a comparison unit having at least two inputs and an output, said first input being connected to said first output of the marker line reversible counter, and said output being connected to said third input of the digital-analog converter;

a first OR element having at least two inputs and an output, said first input being connected to said second output of the marker line coordinate reversible counter;

a second OR element having at least two inputs and an output, said first input being connected to said third output of the marker line coordinate reversible counter;

an image frame reversible counter having at least two inputs and an output, said first input being connected to said output of the first OR element, and said second input being connected to said output of the second OR element;

a digital indication unit having at least two inputs, said first input being connected to said output of the image frame reversible counter, and said second input being connected to said first output of the marker line coordinate reversible counter;

an address unit comprising:

a third OR element having at least two inputs and an output, said first input being connected to said fourth output of the synchronizing generator, said second input being connected to a first output of the scanning device;

a fourth OR element having at least two inputs and an output, said first input being connected to said fifth output of the synchronizing generator, said second input being connected to a second output of said scanning device;

a recording reversible counter having at least two inputs and three outputs, said first input being connected to said output of the third OR element, said second input being connected to said output of the fourth OR element, said first output being connected to said second input of the first OR element, and said output being connected to said second input of the second OR element;

a switch having at least four inputs and an output, said first input being connected to said output of the gating pulse generator, said second input being connected to said output of the reversible recording counter, and said output being connected to said third input of said memory;

an address code rewrite unit having at least two inputs and an output, said first input being connected to said third output of the recording reversible counter;

a readout counter having at least two inputs and two outputs, said first input being connected to said output of the address code rewrite unit, said second input being connected to said sixth output of the synchronizing generator, said first output being connected to said third input of the switch, and said second output being connected to said second input of the comparison unit;

a rewrite signal generator having at least three inputs and an output, said first input being connected to said seventh output of the synchronizing generator, said second input being connected to a first output of the scanning device, said third input being connected to a second output of said scanning device, and said output being connected to said second input of the address code rewrite unit;

an image element counter having at least two inputs and an output, said first input being connected to said output of the gating pulse generator, said second input being connected to said output of the variable frequency pulse generator, and said output being connected to said fourth input of the switch.

* * * * *